(12) United States Patent
Webster et al.

(10) Patent No.: US 6,316,476 B1
(45) Date of Patent: *Nov. 13, 2001

(54) HETEROCYCLIC COMPOUNDS WITH ANTIBACTERIAL AND ANTIMYCOTIC PROPERTIES

(75) Inventors: John M. Webster, North Vancouver; Jianxiong Li, Port Moody; Genhui Chen, Burnaby, all of (CA)

(73) Assignee: Welichem Biotech Inc., Burnaby (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/685,211

(22) Filed: Jul. 23, 1996

Related U.S. Application Data

(63) Continuation of application No. 08/420,307, filed on Apr. 11, 1995, now abandoned.

(51) Int. Cl.[7] .......................... C07D 285/01; C12P 17/18; A01N 43/82

(52) U.S. Cl. .......................... 514/360; 435/119; 548/123
(58) Field of Search .......................... 435/117; 548/123; 514/360

(56) References Cited

FOREIGN PATENT DOCUMENTS

| WO 84/01775 | 5/1984 | (WO) . |
| WO 94/26750 | 11/1994 | (WO) . |
| WO 94/28001 | 12/1994 | (WO) . |

OTHER PUBLICATIONS

C.A. 121:55953 (1994) Takahashi et al CA2106443 (Mar. 19, 1994).*
Akhurst, R. J. and N. E. Boemare "A numerical Taxonomic Study of the Genus Xenorhabdus (Enterobactereacea) and Proposed Elevation of the Subspecies of *X. nematophilus* to Species" *J. Gen. Microbiol.* vol. 134, 1835–1845 (1988).
American Phytopathological Society. Methods for Evaluating Pesticides for Control of Plant Pathogens. St. Paul. Ma, (1986).
Chen, G., G. B., Dunphy, and J. M., Webster, "Antimycotic Activity of Two Xenorhabdus Species and *Photohabdus liminescens*. Bacteria Associated with the Nematodes Steinernema Species and *Heterorhabditis megidis*". *Biol. Control*, Vol. 4, 157–161 (1994).
Li et al. "Antimicrobial Metabolites from a Bacterial Symbiont" *J. Nat. Proc.* vol.58:1081–1085 (1995).
Maxwell et al. "Stability and Activities of Antibiotics Produced during Infection of the insect *Galleria mellonella* by Two Isolates of *Xenorhabdus nematophilus*"*Appl. Environ. Microbiol.* vol. 60, 715–721 (1994).

McInerney et al. "Biologically Active Metabolites from Xenorhabdus spp., Part 1. Dithiolopyrrolone Derivatives with Antibiotic Activity" *J. Nat. Prod.* vol. 54, 774–784 (1991a).
McInerney et al. "Biologically Active Metabolites from Xenorhabdus spp., Part 2. Benzopyran–1–one Derivatives with Gastroprotective Activity" *J. Nat. Prod.* vol. 54, 785–795 (1991b).
National Committee for Clinical Laboratory Standards. Methods for Dilution of Antimicrobial Suscepibility Test for Bacteria That Grow Aerobically. Approved standards M–7A2. National Committee for clinical Laboratory Standards, Villaniova, Pa. (1990).
Paul et al., "Antibiotics in Microbial Ecology: Isolation and Structure Assignment of Several New antibacterial Compounds from the Insect–Symbiotic Bacteria Xenorhabdus spp." J. Chem. Ecol. vol. 7, 589–597 (1981).

(List continued on next page.)

*Primary Examiner*—Herbert J. Lilling
(74) *Attorney, Agent, or Firm*—Klarquist Sparkman, LLP

(57) ABSTRACT

The invention is drawn to novel antibiotics, XENORXIDES of formula shown below, wherein $R_1$, $R_2$=hydrogen, substituted or unsubstituted alkyl, cycloalkyl, acyl, aryl, aralkyl, or heterocyclyl group; $R_3$=hydrogen, alkyl cycloalkyl, aralkyl or aryl group,

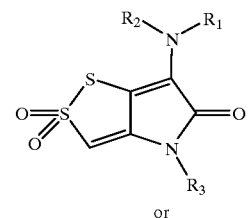

FIG. 1A or

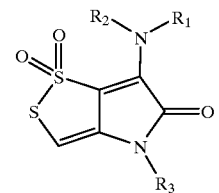

FIG. 1B produced by bacterial symbiont *Xenorhabdus bovienii* and/or other Xenorhabdus species, and/or by oxidation of the corresponding dithiolopyrrolone derivatives with oxygen and Xenorhabdus species, and/or its cell-free filtrate, the additional salts thereof, the compositions thereof and their use as medicaments and/or agrochemicals, particularly in the treatment of infectious diseases involving microorganisms susceptible to them, including drug-resistant Staphylococcus.

7 Claims, 1 Drawing Sheet

OTHER PUBLICATIONS

Putz et al. "Development and Application of Oligonucleoides Probes for Molecular Identification of Xenorhabdus Species" *Appl. Environ. Microbiol.* vol. 56, 181–186 (1990).

Richardson et al., "Identification of an Anthraquinone pigment and a Hydroxystilbene Antibiotic from Xenorhabdus" *App. Environ. Microbiol.* vol. 54, 1602–1605 (1988).

U.S. application No. 08/281,488, Chen et al., filed Jul. 1994.

Akhurst & Boemare "A Numerical Taxonomic Study of the Genus Xenorhabdus (Enterbacteriacae) and Prosed Elevation of the Subspecies of *X. nematophilus* to Species" J. Gen. Microbiol. B4:1835–1845. (1988).

American Phytopathologyical Society, Methods for Evaluating Pesticides for Control of Plant Pathogens. St. Paul. Ma (1985).

Chen et al. "Antimyeotie Activity of Two Xenorhabdus Species and *Photohabelus lumenescens*, Bacteria Associated With the Nematodes Steinernema Species and *Heterorherbolitis megiolis*, " Biol. Control 4:157–161 (1994).

Li et al. "Antimicrobiol Metabolites From a Bacterial Symbiort" J. Nat. Prod. (Accepted) 1995.

Maxwell et al. "Stability and Activitges of Antibiotics Produced During Infection of the Insect Bacteria Mellonella by Two Isolates of *Xenorhabdus nematophilus*" Appl. Environ. Microbiol. 60:715–721 (1990).

McInerney et al. "Biologically Active Metabiolites From Xenorhabdus Spp. Part 1. Diehiolopyrrolene Derivatives With Antibiotic Activity" J. Nat. Prod. 54:774–784. (1991).

McInerney et al. "Biologically Active Metabolites From Xenorhabdus Spp. Part 2. Benzopyran–Tone Derivatives With Gastroprotective Activity" J. Nat. Prod. 54:785–795 (1991).

National Committee for Clinical Laboratory Standards. Methods for Dilution of Antimicrobiol Susceptibility Tests for Bacteria that Grow Aerbically. M–7A2. National Committee For Clinical Laboratory Standards. Pa 49901.

Paul et al. "Antibiotics in Microbiol Ecology: Isolation and Structure Assignment of Several New Antibacterial Compounds From the Insect—Symbiotic Bacteria Xenorharbdus Spp." J. Chem. Ecol. 7:589–597 (1981).

Putz et al. "Development and Application of Oligomicleotide Probes for Molecules Identification of Xenorharbdus Species" Appl. Environ. Microbiol 56:181–186 (1990).

Richardson et al. "Identification of an Tonthraqarinone Pigment and a Hydroxystilbene Antibiotic From Xenorhabdus" App. Environ. Microbiol. 54:1602–1605. (1988).

* cited by examiner

HETEROCYCLIC COMPOUNDS WITH ANTIBACTERIAL AND ANTIMYCOTIC PROPERTIES

This application is a continuation of Ser. No. 08/420307 filed Apr. 11, 1995 now abandoned.

FIELD OF THE INVENTION

The present invention relates to the novel antibiotics, XENORXIDES, which may be obtained by cultivation of Xenorhabdus spp. or by oxidation of the corresponding dithiolopyrrolone derivatives with oxygen and/or Xenorhabdus species, and/or its cell-free filtrate.

SUMMARY OF THE INVENTION

The present invention provides the novel antibiotic XENORXIDES having antimicrobial activity. The present invention also provides methods for the production of XENORXIDES, comprising the step of cultivating the microorganism X. bovienii or oxidation of the corresponding dithiolopyrrolone derivatives with oxygen and Xenorhabdus species, and/or its cell-free filtrate. The present invention further provides novel antimicrobial compositions comprising XENORXIDES, the additional salts thereof, and methods of using the inventive compounds as antibacterial and antimycotic agents.

BRIEF DESCRIPTION OF THE DRAWING

1. The following

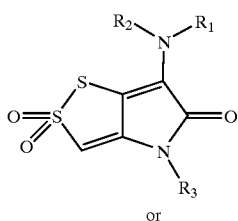

FIG. 1A or

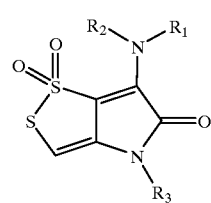

Figure 1:
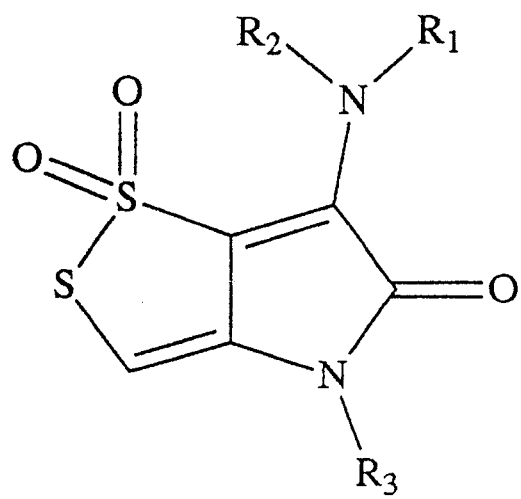
FIG. 1 represents the structural formula of XENORXIDES, a novel group of compounds.
Figure 1:
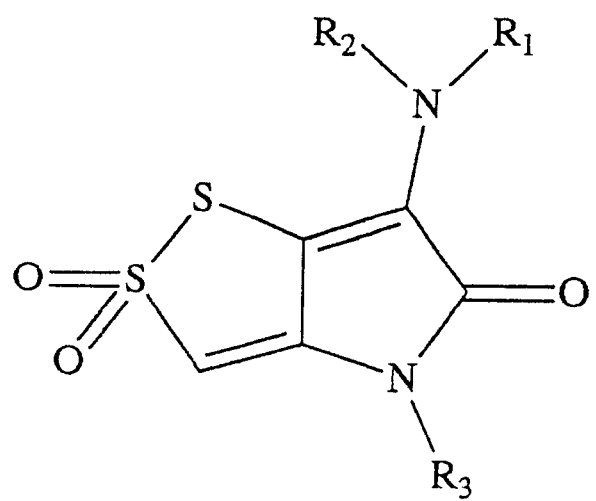

FIG. 1B wherein $R_1$, $R_2$=hydrogren, substituted or unsubstituted alkyl, cycloalkyl, acyl, aryl, aralkyl, or heterocyclyl group; $R_3$=hydrogen, alkyl, cycloalkyl, aralkyl or aryl group.

BACKGROUND

Protection of humans, agricultural crops, stored foods, gardens, ornamental plants, trees and wood products, and animals from bacterial and fungal diseases and the sterilizing of medicinal instruments is extremely important. Unfortunately, bacteria and fungi continue to be problematic pathogens for humans because of the increasing occurrence of strains which are resistant to commonly used antibiotics. Such resistant strains lead to a constant need for new antibacterial and antimycotic substances. As well, the withdrawal of many pesticides from use, for environmental and health reasons, has greatly increased the need for new antifungal and antibacterial agents in the agro-forest industries.

Although there are a limited number of publications on Xenorhabdus and Photorhabdus, it has been recognized that active, antibacterial and antimycotic substances are produced by Xenorhabdus species and Photorhabdus species. Some of these specific compounds have been isolated, identified and their structures elucidated (Li et al., "Antimicrobial metabolites from a bacterial symbiont" J. Nat. Prod. Vol. 58, 1081–1086 (1995); Paul et al., "Antibiotics in Microbial Ecology: Isolation and Structure Assignment of Several New Antibacterial Compounds from the Insect-Symbiotic Bacteria Xenorhabdus spp." J. Chem. Ecol. Vol. 7, 589–597 (1981); Richardson et al., "Identification of an Anthraquinone Pigment and a Hydroxystilbene Antibiotic from Xenorhabdus" App. Environ. Microbiol. Vol. 54, 1602–1605 (1988);. McInerney et al. "Biologically Active Metabolites from Xenorhabdus spp., Part 1. Dithiolopyrrolone Derivatives with Antibiotic Activity" J. Nat. Prod. Vol. 54, 774–784 (1991a); McInerney et al. "Biologically Active Metabolites from Xenorhabdus spp., Part 2. Benzopyran-1-one Derivatives with Gastroprotective Activity" J. Nat. Prod. Vol. 54, 785–795 (1991b)). Recently, the cell-free culture broths of Xenorhabdus species and Photorhabdus luminescens, bacterial symbionts carried by nematodes of the genus Steinernema and Heterorhabditis, respectively were found to be active against many fungi of agricultural and medicinal importance Chen et al., Antimycotic activity of two Xenorhabdus species and P. luminescens, bacteria associated with the nematodes Steinernema species and Heterorhabditis megidis. Biological Control. Vol. 4, 157–162(1994)). However, XENORXIDES, as a novel group of chemicals and the importance of these specific purified metabolites as extremely potent antibacterial and antimycotic agents has heretofore been undiscovered, and are the subjects of this invention. Although corresponding dithiolopyrrolone derivatives have been shown to be active against microorganisms, prior art references have not shown the existence of XENORXIDES and the use of XENORXIDES or any operable aspects as antibacterial and antimycotic agents.

DESCRIPTION OF THE INVENTION

The Microorganisms

Xenorhabdus bovienii and its nematode symbiont Steinernema feltiae used in this study were collected from soil in British Columbia, Canada and maintained in culture in Dr. J. M. Webster's laboratory in the Department of Biological Sciences, Simon Fraser University, Burnaby, B.C., Canada V5A 1S6 (Maxwell et al. 1994). Briefly, last instar larvae of the greater wax moth, Galleria mellonella, were infected with infective juvenile (IJ) nematodes, carrying the X. bovienii A21 strain, at a rate of 25 IJs/larvae. After 24 to 48 h the dead insect larvae were surface disinfected by dipping them into 95% EtOH and igniting them. The cadavers were aseptically dissected, haemolymph was streaked onto an agar culture medium and incubated in the dark at room temperature. The agar medium has the following composition in one liter of distilled water:

beef extract 3 g peptone 5 g bromothymol blue 0.025 g 2,3,5-triphenyltetrazolium 0.04 g Agar 15 g Sterilized at 121° C. for 15 minutes. The resulting primary form of X. bovienii was maintained and subcultured at 14 d intervals. Other sources and depositories of Xenorhabdus species and strains are noted in Akhurst and Boemare "A numerical taxonomic study of the genus Xenorhabdus (Enterobactereacea) and proposed elevation of the subspecies of *X. nematophilus* to species" *J. Gen. Microbiol.* Vol 134, pp.1835–1845 (1988). Putz et al. "Development and application of oligonucleotide probes for molecular identification of Xenorhabdus species" *Appl. Environ. Microbiol.* Vol. 56, 181186 (1990) notes additional sources and depositories, including the American Type Culture Collection, Rockville, Md. Candidate bacterial and fungal pathogens used in bioassays are readily available from many sources, including the American Type Culture Collection, Rockville, Md. For consistency, 14% sucrose lyophilized powder of bacteria stored at −20° C. was frequently used as starting material for cultures. Cultures of *X. bovienii* D strain which have been obtained as above exhibit the following characteristics:

| | |
|---|---|
| Gram reaction | −* |
| Cell size ($\mu$m) | 5.3 × 2.2 |
| Mobility | + |
| Cell peritrichous | + |
| Pigmentation | yellow |
| Catalase | − |
| Oxidase | − |
| Urease | − |
| Lecithinase | + |
| Lipase(Tween 80) | + |
| Acid production | |
| D-Arabinose | +w† |
| Esculine | − |
| D-Fructose | + |
| D-Galactose | − |
| D-Glucose | + |
| Inositol | +w |
| Inulin | − |
| D-Lactose | − |
| D-Maltose | + |
| D-Mannitol | − |
| D-Mannose | + |
| D-Raffinose | − |
| D-Sorbitol | +w |
| L-Sorbose | − |
| D-xylose | − |
| Utilization of carbon sources | |
| Asparagine | + |
| Cystine | − |
| Glysine | − |
| Tyrosine | + |
| Nictinic acid | − |
| Ethanol | − |
| Methanol | − |
| Inositol | +w |
| Mannose | + |
| D-Galatose | − |
| D-Glucose | + |
| D-Lactose | − |
| D-Manitol | − |
| D-Sorbitol | − |
| Ribose | + |

*+ positive; − negative; †+w: weakly positive.

These characteristics are in agreement with those described for *Xenorhabdus bovienii* by Akhurst, R. J. and N. E. Boemare, *J. Gen. Microbiol.* Vol. 134, 1835–1845 (1988), and, therefore, establishes the identity of the organism as *Xenorhabdus bovienii*.

Production of XENORXIDES

Cultivation of the microorganism *X. bovienii* yields the novel antimicrobial substances, XENORXIDES. XENORXIDES may be formed as metabolites thereof.

To prepare XENORXIDES, *X. bovienii* may be cultivated (fermented), for example, at about 25° C. under submerged aerobic conditions in an aqueous nutrient medium containing assimilable carbon (carbohydrate) and nitrogen sources until antibiotic activity due to XENORXIDES is imparted to the medium. The fermentation may be carried out for a time period such as approximately 48 to 96 hours, at the end of which time the antibiotic XENORXIDES have been formed, and may be isolated from the fermentation medium and purified.

After the fermentation has been completed, the fermented broth may be filtered or centrifuged and the pH of the filtrate adjusted to about 7.0 by the addition of hydrochloric acid or kept as it was. The filtrate may then be extracted with a water immiscible organic solvent, for example, with ethyl acetate or chloroform. The combined organic layers (e.g. pooled ethyl acetate or chloroform extracts) may be concentrated in vacuum (e.g. at about 30° C.) to an oily residue ("syrup"). The oil may be mixed with a small amount of organic solvent and chromatographed on a silica gel column. After introduction of the sample, chloroform or other organic solvent may be applied to elute the bioactive fraction out. The bioactive fraction may be purified further by high resolution liquid chromatography (HPLC) with organic and/ or aqueous solution.

XENORXIDES are difficult to detect in the culture broth of *X. bovienii*, but the corresponding dithiolopyrrolone derivatives are present in relatively large amounts. Therefore, the culture broth of *X. bovienii*, with corresponding dithiolopyrrolone derivatives present in relatively large amounts, may be filtered or centrifuged. The cell-free filtrate may be open to the air for extended periods from one week up to one month with or without stirring at room temperature or other temperature. This process may oxidize all or part of the corresponding dithiolopyrrolone derivatives to XENORXIDES, thus providing a practical way to produce XENORXIDES.

The Antibiotic and Use Thereof

XENORXIDES possess antibacterial and antimycotic properties, and have been found to have the characteristics shown in the FIG. 1 and in the Examples herein.

The compounds of the present invention include XENORXIDES and the additional salts thereof. It is preferred that the inventive compounds have a degree of purity such that they are suitable for use as antibiotic agents. A particularly preferred embodiment of the instant invention provides XENORXIDES in a substantially pure state. The substantially pure compounds are preferably employed in the compositions and methods described following.

The inventive compounds are useful as antimicrobial agents, useful in inhibiting the growth of microorganisms, particularly as an antibiotic drug, useful in treating bacterial infection caused by antibiotic resistant bacteria such as Gram positive bacteria, e.g. bacteria of the genera Bacillus and Staphylococcus, useful in treating infection caused by fungi and yeasts of the genera Aspergillus, Botrytis and Cryptococcus. Inhibition of the growth of a bacterium or fungus may be achieved by contacting the organism with a compound of the present invention in an amount effective there.

Thus, the compounds of the present invention may be employed in utilities suitable for antibacterial and antimycotic agents.

The inventive compounds may, for example, be used in treating a host infected with a bacterium and/or fungus, comprising the step of administering to the host XENORXIDE(S) or a physiologically tolerated salt thereof in an amount effective for the treatment. Treatment of such infections according to the instant invention includes both mitigation as well as elimination thereof.

Hosts treatable according to the method of the present invention include plants and animals, particularly mammals such as dogs, cats and other domestic animals and, especially, humans. The dosage form and mode of administration, as well as the dosage amount, may be selected by the skilled artisan. The dosage amount will vary with the severity of the infection, and with the size and species of the host. Exemplary daily dosages for an adult human are those within the range of about 2.5 mg to about 2,000 mg/day. Administration to a mammalian host may, for example, be oral, parenteral, or topical. Administration to a plant host may be accomplished, for example, by application to seed, foliage or other plant part, or to the soil.

Compositions are also provided by the present invention which comprise XENORXIDE(S) and/or the additional salts thereof in an amount effective for the treatment of infection by a microorganism, and a physiologically tolerated vehicle or diluent. The term "physiologically tolerated" is equivalent to the term "pharmaceutically acceptable" when used in reference to the treatment of a mammalian host. The appropriate solid or liquid vehicle or diluent may be selected, and the compositions prepared, by methods known to the skilled artisan. Treatment of simultaneous infections by more than one bacterium and/or fungus is, or course, contemplated.

The inventive compounds may be employed also as antibacterial and antimycotic agents useful in inhibiting the growth of microorganisms present or eradicating microorganisms on a surface or in a medium outside a living host. The present invention, therefore, provides a method for inhibiting the growth of at least one microorganism present on a surface or in a medium, comprising the step of contacting the surface or medium with XENORXIDE(S) in an amount effective for the inhibition. Thus, the inventive compounds may be employed, for example, as disinfectants for a variety of solid and liquid media susceptible to microbial growth. Suitable amounts of the inventive compounds may be determined by methods known to the skilled artisan. Compositions comprising XENORXIDE(S) in an amount effective for inhibiting the growth of at least one bacterium, and a vehicle or diluent, are also provided by the present invention.

For agricultural application, the bactericidal and fungicidal compositions may be formed using one of the active ingredients in an inert carrier. If formulated as a solid, the ingredients may be mixed with typical carriers such as Fuller's earth, kaolin clays, silicas or other wettable inorganic diluents. Free-flowing dust formulations may also be utilized by combining the dry active ingredient with finely divided solids such as talc, kieselguhr, pyrophyllite, clays, diatomaceous earth and the like.

The powders may also be applied as a suspension or solution, depending on the solubility in the liquid carrier. Pressurized sprays, typically aerosols with the active ingredient dispersed in a low-boiling dispersant solvent carrier, may be used. Percentages of weight may vary according to the manner in which the composition is to be applied, and formulation used. In general, the active ingredient will comprise 0.005% to 95% of the active ingredient by weight in the bactericidal and fungicidal composition. The bactericidal and fungicidal composition may be applied with other ingredients, including growth regulators, insecticides, fertilizers, and the like. Formulation of the active ingredients to assist applicability, ease handling, maintain chemical stability and increase effectiveness may require addition of various materials. Solvents may be chosen on the basis of affecting the solubility of the active ingredient, fire hazard and flash point, emulsifiability, specific gravity and economic considerations. Adjuvants may be added to enhance the active ingredients, and can include surfactants which are anionic, cationic or nonionic. Stabilizers and antifreeze compounds will prolong storage. Additionally, synergists, stickers, spreaders and deodorant compounds can be added to improve the handling characteristics of the commercial formulation. Alternatively, the active ingredient can be combined with an inert carrier, such as calcium carbonate, and formed into a pill or other consumable delivery device, including controlled release devices intended to deliver metered doses of the active ingredient.

The following examples are provided to further illustrate the invention, and are not intended to in any way limit the scope of the instant claims.

EXAMPLE 1

Preparation of Xenorxides

A. Isolation of Xenorxides from the Cultural Broth of *X. bovienii*

Cultures were shaken at 180 rpm on an Eberbach gyrorotary shaker for 24 h at 25° C. Bacterial fermentation was initiated by adding 100 ml of this bacterial culture to 900 ml of tryptic soy broth in a 2,000 ml flask. The flask was incubated in the dark at 25° C. on a gyrorotary shaker. After 96 h, the culture was immediately centrifuged (12,000 g, 20 minutes, 4° C.) to separate the bacterial cells. The cell-free broth was then extracted with ethyl acetate 4 times. The combined extracts were dried with anhydrous sodium sulfate and then filtered through filter paper. The filtrate was concentrated on a rotary evaporator below 30° C. under vacuum to yield a brown oil. After the above experiment was repeated 10 times, approximately 3 g of the oil was obtained. The crude extracts were then loaded onto a silica gel (200 g silica gel 60, 40 cm×5 cm, EM Science, Darmstadt, Germany) chromatographic column. The yellow bioactive fraction was eluted out with ether or ethyl acetate. This bioactive fraction was then subject to HPLC on a $C_{18}$ preparative column (Spherisorb 10 (ODS(1)), 250×10 mm, 10 micro, Phenomenex, Torrance, Calif.) with a program (isocratic at 10% acetonitrile in water for 5 min, then gradually increasing to 85% acetonitrile in 35 min, isocratic for 5 min, then decreasing back to 10% in 2 min) at 2.5 min. The eluate was monitored at 254 nm. XENORXIDE 1(about 0.3 mg per liter of the cultural broth) was eluted at 33.6 min, and XENORXIDE 2(0.2 mg/l) was eluted at 35.2 min.

B. Preparation of Xenorxides from *X. bovienii*

The cell-free broth was obtained using the same method as described above, and was then stored at 4° C. to room temperature for 3 to 6 weeks. Then the aqueous broth was extracted with ethyl acetate, and the combined extracts were separated using the same process discussed above. XENORXIDE 1 was eluted at 33.6 min (2 mg/l), XENORXIDE 2 was eluted at 35.2 min (1.5 mg/l).

C. Identification of the Active Components from *X. bovienii*

NMR spectra were recorded on a Bruker WM400 spectrometer in $CDCl_3$, using residual $CDCl_3$ (~7.25) as internal standard. Low resolution mass spectra were obtained on a Hewlett-Packard 5985B GC/MS system operating at 70 eV using a direct probe. High resolution MS spectra were recorded on a Kratos MS80 instrument. IR spectra were recorded as neat film on NaCl using a Perkin-Elmer 599B spectrometer. (Abbreviations used as follows: EI=Electron Impact, M+=Molecular Ion, t=triplet, J=coupling constant, Hz=Hertz, d=doublet, m=multiplet, bs=broad singlet).

XENORXIDE 1: EIMS: 317(2), 316(M+, 13), 220(9), 219(9), 218(100), 186(23), 154(16), 99(40), 71(39); HRMS: 316.0555 (Calc. for $C_{12}H_{16}N_2O_4S_2$: 316.0551, 20), 217.9824 (Calc. for $C_6H_6N_2O_3S_2$: 217.9820, 100), 154.0197 (Calc. for $C_6H_6N_2OS$: 154.0201, 16); IR (KBr): 3448, 3298, 3275, 1720, 1686, 1654, 1637, 1560, 1522, 1310, 1139, 551 $cm^{-1}$; $^1$HNMR ($CDCl_3$) δ: 7.56(1H, bs,CO—NH), 6.35 (1H, s, H-3), 3.20 (3H, s, N—Me), 2.38 (2H, t, CO—$CH_2$, J=7.4 Hz), 1.67 (2H, m, $CH_2$), 1.32 (4H, m, $CH_2CH_2$), 0.89 (3H, t, J=7.0 Hz); $^{13}$CNMR ($CDCl_3$) δ: 171.6(s, CON), 164.7 (s, CO), 145.4(s, $C_7$), 121.3(s, $C_6$), 116.2(s, $C_8$), 109.2(d, $C_3$), 36.4, 31.2, 27.8, 24.6, 22.3, 13.8.

XENORXIDE 2: EIMS: 330(M+, 10), 218(100); HRMS: 330.0707 (Calc. for $C_{13}H_{18}N_2O_4S_2$: 330.0708, 18), 217.9829 (Calc. for $C_6H_6N_2O_3S_2$: 217.9820, 100), 154.0213 (Calc. for $C_6H_6N_2OS$: 154.0201, 16);; IR (KBr): 3438, 3298, 1719, 1686, 1654, 1637, 1560, 1522, 1400, 1310, 1142, 551 $cm^{-1}$; $^1$HNMR ($CDCl_3$) δ: 7.56 (1H, bs,CO—NH), 6.35 (1H, s, H-3), 3.20 (3H, s, N—Me), 2.36 (2H, t, CO—CH2, J=7.4 Hz), 1.67 (2H, m, CH2), 1.2–1.6 (1H, m, CH), 1.22 (2H, m, $CH_2$), 0.89 (6H, d, J=6.6 Hz); Different NOE experiment showed the NOE effect between the peak at 6.35 ppm and 3.20 ppm; $^{13}$CNMR ($CDCl_3$) δ: 171.6(s, CON), 164.7 (s, CO), 145.4(s, $C_7$), 121.3(s, $C_6$), 116.2(s, $C_8$), 109.2(d, $C_3$), 38.2(t, $CH_2$), 36.7(t, $CH_2$), 28.0(q, $CH_3$), 27.8(d, CH), 22.8(t, $CH_2$) 22.4(q, $CH_3$).

EXAMPLE 2

Xenorxides as Antibiotic

The Following Experiments were Conducted, Demonstrating the Antibiotic Properties of Xenorxides To determine minimum inhibitory concentration (MIC) of the Xenorxides, the standard procedures (The National Committee for Clinical Laboratory Standards and Methods for Evaluating Pesticides for Control of Plant Pathogens of the American Phytopathological Society) for testing antibiotics was followed. Briefly, test chemicals were dissolved in dimethyl sulphoxide (DMSO), filter sterilized and diluted into with distilled water resulting in a final DMSO concentration <0.4%(v/v) at a chemical stock concentration of 200 μg The active compounds were serially diluted by twofold (or mixed with equal amount of media/agar) to produce culture media containing the compound from 100 μg/ml to 0.1 μg/ml (i.e. 100, 50, 25, 12.5, 6.3, 3.2, 1.6, 0.8, 0.4, 0.2, 0.1) for the determination of MICs. Test bacteria and the test yeast (*Cryptococcus neoformans*) were grown on nutrient agar (potato dextrose agar for the yeast) for 24 h (35° C.), then were scraped from the plate by flooding the plate with 0.8% saline and diluted with the saline to make inocula (containing 2.5–2.8×$10^7$ cells/ml). Aspergillus spp. and *Botrytis cinerea* were grown on potato dextrose agar for 7d (25° C.) before the conidia were harvested by flooding the plate with sterile, distilled water and diluted to make the final inocula(2.5–3.0×$10^6$ conidia/ml). The inoculated test media were incubated at 35° C. (*B. cinerea* 24° C.) and the MICs were visually determined after 24 h incubation(2d for *B. cinerea*). The minimum inhibitory concentration is defined as the lowest chemical concentration which prevents the growth of the test organism at the above conditions.

It was found that similar results were obtained from both liquid and agar culture methods. Table 1 shows the MICs determined for the compounds against each microorganism. In conclusion, it is shown that Xenorxides, isolated from Xenorhabdus have potent antimicrobial properties, in particularly against some antibiotic resistant Staphylococcus strains.

TABLE 1

Minimum Inhibitory Concentrations (MIC) of antibiotics isolated from Xenorhabdus species on bacteria and fungi.

| | MICs (μg/ml) | |
|---|---|---|
| Organisms | XENORXIDE 1 | XENORXIDE 2 |
| Bacillus subtilis | 6 | 6 |
| Micrococcus luteus | 25 | 6 |
| Staphylococcus aureus ATCC 29213 | 6 | 6 |
| S. aureus 0012* | 3 | 3 |
| S. aureus 0017* | 3 | 1.5 |
| Aspergillus fumigatus ATCC 13073 | 0.75 | 1.5 |
| Aspergillus flavus ATCC 24133 | 0.75 | 1.5 |
| Botrytis cinerea | 12 | 25 |
| Cryptococcus neoformans ATCC 14117 | 6 | 6 |

*clinical isolates of multi-antibiotic-resistant isolates, provided by S. Farmer of the Canadian Bacterial Diseases Network, Vancouver, British Columbia, Canada.

While our above description contains many specificities, these should not be construed as limitations on the scope of the invention, but rather as examples of preferred embodiments. Accordingly, the scope of the invention should not be determined by the embodiments presented, but by the appended claims and their legal equivalents.

References Cited

Publications
1. Akhurst, R. J. and N. E. Boemare "A numerical Taxonomic Study of the Genus Xenorhabdus (Enterobactereacea) and Proposed Elevation of the Subspecies of *X. nematophilus* to Species" *J. Gen. Microbial.* Vol 134, 1835–1845 (1988).
2. American Phytopathological Society. Methods for Evaluating Pesticides for Control of Plant Pathogens. St. Paul, Mass., (1986).
3. Chen, G., G. B., Dunphy, and J. M., Webster. "Antimycotic Activity of Two Xenorhabdus Species and *Photorhabdus luminescens*, Bacteria Associated with the *Nematodes Steinernema* Species and *Heterorhabditis megidis*". *Biol. Control*, Vol. 4, 157–161 (1994).
4. Li et al. "Antimicrobial Metabolites from a Bacterial Symbiont" *J. Nat. Prod.* Vol. 58, 1081–1085 (1995).
5. Maxwell et al. "Stability and Activities of Antibiotics Produced during Infection of the Insect *Galleria mellonella* by Two Isolates of *Xenorhabdus nematophilus*" *Appl. Environ. Microbiol.* Vol. 60,715–721 (1994).
6. McInerney et al. "Biologically Active Metabolites from Xenorhabdus spp., Part 1. Dithiolopyrrolone Derivatives with Antibiotic Activity" *J. Nat. Prod.* Vol. 54, 774–784 (1991a).
7. McInerney et al. "Biologically Active Metabolites from Xenorhabdus spp., Part 2. Benzopyran-1-one Derivatives with Gastroprotective Activity" *J. Nat. Prod.* Vol. 54, 785–795 (1991b).
8. National Committee for Clinical Laboratory Standards. Methods for Dilution of Antimicrobial Susceptibility Tests for Bacteria That Grow Aerobically. Approved standards M-7A2. National Committee for clinical Laboratory Standards, Villaniova, Pa. (1990).
9. Paul et al., "Antibiotics in Microbial Ecology: Isolation and Structure Assignment of Several New antibacterial Compounds from the Insect-Symbiotic Bacteria Xenorhabdus spp." J. Chem. Ecol. Vol. 7,589–597 (1981).
10. Putz et al. "Development and Application of Oligonucleotide Probes for Molecular Identification of Xenorhabdus Species" *Appl. Environ. Microbial.* Vol. 56, 181–186 (1990).

11. Richardson et al., "Identification of an Anthraquinone pigment and a Hydroxystilbene Antibiotic from Xenorhabdus" *App. Environ. Microbiol.* Vol. 54, 1602–1605 (1988)

What is claimed is:

1. A compound of the following structure:

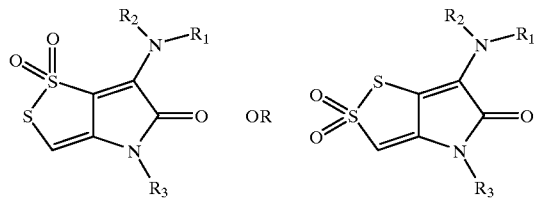

wherein, $R_1$=hydrogen, alkyl, cycloalkyl, acyl, aryl, or aralkyl;
$R_2$=hydrogen, alkyl, cycloalkyl, aryl, or aralkyl; and
$R_3$=alkyl, cycloalkyl, aryl, or aralkyl.

2. The compound of claim 1 wherein,
$R_1$=acyl;
$R_2$=hydrogen; and
$R_3$=alkyl.

3. The compound of claim 1 wherein,
$R_1$=$CH_3(CH_2)_4CO$;
$R_2$=hydrogen; and
$R_3$=$CH_3$.

4. The compound of claim 1 wherein,
$R_1$=$(CH_3)_2CH(CH_2)_3CO$;
$R_2$=hydrogen;
$R_3$=$CH_3$.

5. A composition for treatment of an infection by a microorganism, comprising the compound of claim 1 and a physiologically tolerated vehicle or diluent.

6. A composition for treatment of an infection by a microorganism, comprising the compound of claim 3 and a physiologically tolerated vehicle or diluent.

7. A composition for treatment of an infection by a microorganism, comprising the compound of claim 1 and a physiologically tolerated vehicle or diluent.

* * * * *